(12) United States Patent
Ulrichsen et al.

(10) Patent No.: US 6,914,678 B1
(45) Date of Patent: Jul. 5, 2005

(54) INSPECTION OF MATTER

(75) Inventors: Børre Bengt Ulrichsen, Oslo (NO); Jon Henrik Tschudi, Oslo (NO); Ib-Rune Johansen, Oslo (NO)

(73) Assignee: Titech Visionsort AS, Oslo (NO)

( * ) Notice: Subject to any disclaimer, the term of this patent is extended or adjusted under 35 U.S.C. 154(b) by 0 days.

(21) Appl. No.: 09/936,924

(22) PCT Filed: Mar. 20, 2000

(86) PCT No.: PCT/IB00/00301

§ 371 (c)(1),
(2), (4) Date: Jun. 21, 2002

(87) PCT Pub. No.: WO00/57160

PCT Pub. Date: Sep. 28, 2000

(30) Foreign Application Priority Data

Mar. 19, 1999 (GB) .............................. 9906326
Sep. 20, 1999 (GB) .............................. 9922140

(51) Int. Cl.[7] .............................................. G01N 21/84
(52) U.S. Cl. ..................................................... 356/429
(58) Field of Search ............................... 356/429–431, 356/237.1–237.2, 239.1, 239.4, 240.1, 601, 613, 625, 628; 209/576, 577, 580, 587, 588, 639, 936, 938; 250/301, 225, 223 R

(56) References Cited

U.S. PATENT DOCUMENTS 5,676,256 A * 10/1997 Kumar et al. ................ 209/580
5,770,864 A * 6/1998 Dlugos .................. 250/559.19
6,060,677 A * 5/2000 Ulrichsen et al. ........... 209/577
6,353,197 B1 * 3/2002 Ulrichsen et al. ........... 209/577
6,509,537 B1 * 1/2003 Krieg et al. ................. 209/579

FOREIGN PATENT DOCUMENTS

| DE | 3242447 A1 | 5/1984 |
| WO | WO96/06689 | 3/1996 |
| WO | WO98/44335 | 10/1998 |

* cited by examiner

Primary Examiner—Michael P. Stafira
(74) Attorney, Agent, or Firm—Reising, Ethington, Barnes, Kisselle, P.C.

(57) ABSTRACT

Apparatus for automatically inspecting a stream of matter comprises lamps which emit a detection medium, such as IR or visible light, to be active at the matter, a rotary polygonal mirror which receives from a multiplicity of detection zones at the matter detection medium which has been varied by variations in the matter, an optical detection device which receives the varied medium by reflection from the mirror, to detect a plurality of wavelengths of the varied medium substantially simultaneously, and to generate detection data in respect of that plurality of wavelengths substantially simultaneously and in dependence upon the variations in the medium, and a microprocessor which obtains the detection data from the device. The beams of the varied medium which are received at the device and emanate from the zones travel along respective paths from the matter to the mirror 9 which paths converge continuously with respect to each other from the matter to the mirror. Those paths may extend to the mirror indirectly by way of at least one planar mirror, or directly to the mirror, in which latter case the axis of the mirror would be substantially parallel to the direction of advance of the matter.

59 Claims, 10 Drawing Sheets

INSPECTION OF MATTER

BACKGROUND OF THE INVENTION

1. Field of the Invention

This invention relates to automatically inspecting matter, for example automatic inspection and sorting of discrete objects of differing compositions, e.g. waste objects, or automatic inspection of sheet material, which may be in the form of a strip, for surface layer composition, e.g. surface layer thickness.

With the recent focus on collection and recycling of waste, the cost effectiveness of waste sorting has become an essential economic parameter.

2. Description of Related Art

In the "Dual System" in Germany all recyclable "non-biological" packaging waste excluding glass containers and newsprint is collected and sorted in more than 300 sorting plants.

Objects can be sorted on the basis of:—

Size

Density/weight

Metal content (using eddy current effect)

Ferrous metal content (using magnetic separation)

but most objects such as plastics bottles and beverage cartons are still today sorted out manually to a considerable extent. Some beverage cartons contain an aluminium barrier and by eddy current induction they can be expelled from the waste stream. Generally, beverage cartons in their simpler form present a composite object consisting of paperboard with polymer overcoats on both their inside and outside surfaces.

Several sorting systems exist today that can sort a number of different plastics bottles/objects from each other when they arrive sequentially (i.e. one-by-one). The detection is based on reflected infrared spectrum analysis. To separate the various polymers a quite elaborate variance analysis is performed and thus detection systems become expensive. The objects being fed sequentially pass beneath the infrared spectral detector whereby infrared is shone onto the objects and the relative intensities of selected wavelengths of the infrared radiation reflected are used to determine the particular plastics compound of the plastics passing beneath the detection head. Downstream of the detection head are a number of air jets which blow the individual plastics objects into respective bins depending upon the plastics which constitutes the majority of the object.

A similar system is disclosed in U.S. Pat. No. 5,134,291 in which, although the objects to be sorted can be made of any material, e.g. metals, paper, plastics or any combination thereof, it is critical that at least some of the objects be made predominantly from PET (polyethylene terephthalate) and PS (polystyrene) as well as predominantly from at least two of PVC (polyvinyl chloride), PE (polyethylene) and PP (polypropylene), for example objects including: an object made predominantly from PET, an object made predominantly from PS, an object made predominantly from PVC and an object made predominantly from PE. A source of NIR (Near Infra Red), preferably a tungsten lamp, radiates NIR onto a conveyor sequentially advancing the objects, which reflect the NIR into a detector in the form of a scanning grating NIR spectrometer or a diode array NIR spectrometer. The detector is connected to a digital computer connected to a series of solenoid valves controlling a row of air-actuated pushers arranged along the conveyor opposite a row of transverse conveyors. The diffuse reflectance of the irradiated objects in the NIR region is measured to identify the particular plastics of each object and the appropriate solenoid valve and thus pusher are operated to direct that object laterally from the conveyor onto the appropriate transverse conveyor. The computer can manipulate data in the form of discrete wavelength measurements and in the form of spectra. A measurement at one wavelength can be ratioed to a measurement at another wavelength. Preferably, however, the data is manipulated in the form of spectra and the spectra manipulated, by analogue signal processing and digital pattern recognition, to make the differences more apparent and the resulting identification more reliable.

DE-A-4312915 discloses the separation of plastics, particularly of plastics waste, into separate types, on the basis of the fact that some types of plastics have characteristic IR spectra. In the IR spectroscopic procedure, the intensity of diffusely reflected radiation from each sample is measured on a discrete number of NIR wavelengths simultaneously and the intensities measured are compared. Measurements are taken on wavelengths at which the respective types of plastics produce the minimum intensities of reflected radiation. If, for example, three different plastics are to be separated, each sample is measured on three wavelengths simultaneously, whereby one type of plastics is identified in a first comparison of the intensity of the reflected radiation on the lowest wavelength with that of the second-lowest wavelength and the other two types of plastic are determined in a second comparison of the greater intensity on one wavelength in the first comparison with the intensity on the third wavelength. To measure the light on particular wavelengths, respective detectors can have narrow band pass filters for the respective requisite wavelengths, and respective constituent cables of a split optical fibre cable are allocated to the respective detectors, the cable entry lying in the beam path of a lens for detecting the light reflected from the sample. Alternatively, a light dispersing element, e.g. a prism or grid, is placed in the beam path after the lens and several detectors are arranged to detect the NIR of the requisite wavelengths. Sorting facilities are controlled by utilising the detection data obtained by the comparisons. As a further example, five differing plastics, namely PA (polyamide), PE, PS, PP and PETP, may be separated, utilising measurement points at five differing wavelengths between 1500 nm. and 1800 nm.

EP-A-557738 discloses an automatic sorting method with substance-specific separation of differing plastics components, particularly from domestic and industrial waste. In the method, light is radiated onto the plastics components, or the plastics components are heated to above room temperature, light emitted by the plastics components and/or light allowed through them (in an embodiment in which light transmitted through the components and through a belt conveying them is measured) is received on selected IR wavelengths, and the material of the respective plastics components is identified from differences in intensity (contrast) between the light emitted and/or absorbed, measured on at least two differing wavelengths. The light emitted or allowed through is received by a camera which reproduces it on a detector through a lens. A one-dimensional line detector is usable, although a two-dimensional matrix detector or a one-element detector with a scanning facility can be employed. In order that the camera may receive the light on selected IR wavelengths, interference filters may be mounted either in front of the light source or in front of the lens or the detector. In an example in which the material of the plastics components is identified from the differences in intensity of emitted light at two differing wavelengths, the wavelengths are chosen to produce maximum contrast. This means that one wavelength is selected so that maximum intensity of the emitted light is obtained at a specified viewing angle, whereas the other wavelength is selected so that minimum intensity is obtained at that viewing angle. Changing of wavelengths may be achieved by mounting the filters on a rotating disc, with the frequency of rotation being synchronised with the imaging frequency of the detector. Alternatively, an electrically triggered, tunable, optical filter may be employed. The electrical signals generated by the detector are fed to an electronic signal processor, digitised, and subsequently evaluated by image processing software. It is ensured that the plastics components are at approximately the same temperature at the time of imaging, as differences in contrast can also be caused by temperature differences. The belt should consist of a material which guarantees constant contrast on individual wavelengths.

There is also previously known a system in which infrared spectral detection is performed from below the objects, with the objects passing sequentially over a hole up through which the IR is directed. Again, the infrared reflected is used to sort the objects according to the various plastics within the respective objects.

U.S. Pat. No. 5,260,576 and U.S. Pat. No. 5,339,962 disclose a method and apparatus for distinguishing and separating material items having different levels of absorption of penetrating electromagnetic radiation by utilising a source of radiation for irradiating an irradiation zone extending transversely of a feed path over which the material items are fed or passed. The irradiation zone includes a plurality of transversely spaced radiation detectors for receiving the radiation beams from the radiation source, the detectors receiving the radiation substantially on a direct line from the source. The material items pass through the irradiation zone between the radiation source and the detectors and the detectors measure one or more of the transmitted beams in each item passing through the irradiation zone to produce processing signals which are analysed by signal analysers to produce signals for actuating a separator device in order to discharge the irradiated items toward different locations depending upon the level of radiation absorption in each of the items. The disclosure states that mixtures containing metals, plastics, textiles, paper and/or other such waste materials can be separated since penetrating electromagnetic radiation typically passes through the items of different materials to differing degrees, examples given being the separation of aluminium beverage cans from mixtures containing such cans and plastic containers and the separation of chlorinated plastics from a municipal solid waste mixture. The source of penetrating radiation may be an X-ray source, a microwave source, a radioactive substance which emits gamma rays, or a source of UV energy, IR energy or visible light. One example of material items which are disclosed as having been successfully separated are recyclable plastic containers, such as polyester containers and polyvinyl chloride PVC) containers, which were separated using X-rays. WO-A-95/03139 discloses a similar system which is employed for automatically sorting post-consumer glass and plastics containers by colour.

In an eddy current system for ejecting metal from a stream of waste, the discharge end roller of a belt conveyor normally contains a strong alternating magnetic field generated by permanent magnets contained within and distributed along the roller and counter-rotating relative to the sense of rotation of the roller. This field ejects metallic objects to varying degrees depending upon the amount and the conductivity of the metal of the object. Since metallic objects in which the metal content is small, for example post-consumer packaging cartons of a laminate consisting of polymer-coated paperboard and aluminium foil, are only weakly affected by the magnetic field, such cartons tend not to be separated-out by the eddy-current ejection system.

Another known system uses an electromagnetic field for eddy current detection through induction of eddy currents in the metal in metallic objects and the detection output is used to control an air jet ejection arrangement but this time the objects are caused to queue up one after another in single lines.

WO-A-96/06689 discloses a system for automatically inspecting matter for varying composition and comprising one or more detection stations through which one or more streams of matter are advanced and particular materials therein are detected through their diffusely reflected IR spectra, if any, and/or through their variation of an electromagnetic field by their metallic portions, if any. In one version, a multiplicity of detection points represented by lenses are distributed in a straight line across and below the stream as it passes over a transverse slot through a downwardly inclined plate at the downstream end of a conveyor belt, with a separate light source for each lens. Optical fibres transmit the IR from the respective lenses to a rotary scanner whence a diffuser shines the IR onto infrared filters ahead of IR detectors dedicated to respective wavelengths, to date output of which is utilised in controlling air jet nozzles which separate-out desired portions of the stream. In other versions, a row of light sources distributed across the overall width of one or more belt conveyors may cause desired portions of the stream at detection points distributed in an arc across the stream to reflect light diffusely onto a part-toroidal mirror extending over that overall width, whence the light is reflected, by a rotating, polygonal mirror through optical filters dedicated to differing IR wavelengths, onto detectors the data output of which is utilised in controlling solenoid valves operating air jet nozzles which separate-out the desired portions. Alternatively or additionally, an oscillator and an antenna which extends over that overall width generate an electromagnetic field through the belt and sensing coils sense variations therein produced by metallic portions of the stream passing through the detection station and the detection data produced by the sensing coils is used to control the solenoid valves operating the nozzles to separate-out the metallic portions. In a further version, the rotating, polygonal mirrors are retained and the part-toroidal mirror may be replaced by a mirror comprised of a series of facets or very small mirrors in a horizontal row transverse to the stream, which in this version is a laminate comprised of paperboard onto which a polymer has been extruded. The detection points are arranged in a straight row across the laminate.

JP-A-11-183399 describes a surface-flaw inspection device equipped with multiple camera units arranged one after another widthwise of matter to be inspected, in the form of a zinc-alloy-plated steel plate. Each camera unit incorporates at least two light-receiving cameras which observe the plate under differing optical conditions. The device also includes a processing section which determines the presence or absence of a surface flaw at each position in the width direction of the plate, based on the observation data received from the cameras incorporated in the corresponding camera unit. If the processing section is unable to obtain from a particular camera unit the observation data under all of the required optical conditions, at the boundary between the observation ranges of that camera unit and an adjacent camera unit, it uses the observation data obtained by that adjacent camera unit as the missing observation data to determine the presence or absence of a surface flaw at the boundary. The plate is illuminated by a linear diffusion light source which extends the entire width of the advancing plate. The light shines on to the plate from the light source at, for example, 60° to the vertical, through a cylindrical lens and a deflection board, the deflection angle of which is 45°. The light reflected from the plate travels directly to a mirror and thence to the camera units, which are fixed above the mirror.

CA-A-1219933 discloses the testing a sheet of transparent material, particularly flat glass, for flaws such as foreign substances or gas bubbles trapped in the sheet, in which the sheet is scanned with a flying light spot over its width, and the transmitted and reflected radiation is intercepted, converted into electrical signals, and evaluated. Above the sheet is a receiver for reflected radiation, while below the sheet is a receiver for transmitted radiation, the two receivers being connected to an evaluation unit, which is also connected to photomultipliers facing respective lateral edges of the sheet. In a preferred version, a laser is provided with a beam splitter which reflects a reference partial beam and another partial beam on to a rotary polygonal mirror having its axis substantially parallel to the direction of advance of the sheet. Because of the rotation of the mirror, the partial beams scan the entire width of the sheet, the reference beam being passed over a notched reference strip extending across the sheet. A photoelectric converter is assigned to each of the ends of the reference strip, receives light emerging from the reference strip and passes a corresponding signal to the evaluation unit. If the sheet contains a flaw in the form of a core bubble, the other partial beam no longer reaches the upper receiver but is deflected to the lateral edge face of the sheet, where it enters one or both of the photomultipliers. The reference beam scans the reference strip and enters it at its notches, pulses being produced in the relevant photoconverter(s) by the notches, these pulses being compared in the evaluation unit with corresponding values obtained from the photomultipliers.

U.S. Pat. No. 5,305,894 describes a system for sorting items, such as potato crisps, which computes the geometric centre of any item containing one or more defects and directs an ejection air blast at the geometric centre of the item. Video data from a scanning camera are transmitted to an item processor and a defect processor. The item processor builds in memory an image of every item, whether acceptable or defective, while the defect processor builds a defect list of defect coordinate locations detected only on defective items. The defect processor transmits the defect list to the item processor where the defect list is compared with the stored image of the item. For each defective item, the item processor computes its geometric centre that is added to a defective items list for use by a removal process that actuates air blasts directed towards the centres of defective items. The items may be brought to the removal station by a conveyor which projects the acceptable items on to another conveyor, whilst the air blasts direct downwards the defective items flying across the gap between the two conveyors.

U.S. Pat. No. 5,448,359 discloses an optical distance sensor according to the confocal optical imaging principle for the determination of height values and three-dimensional surface measurement, particularly in the inspection of complex units, for example equipped, printed circuit boards. An illumination beam from a laser passes through a coupling-out mirror on to a rotary polygonal mirror and thence through a scanning objective to the unit being inspected. The illumination beam is reflected from the unit back through the scanning objective and via the polygonal mirror to the coupling-out mirror whence it passes through a beam splitting unit as partial beams on to a plurality of photodetectors. The height level within the depth of focus is recognisable by the photodetector with the greatest light intensity.

U.S. Pat. No. 4,996,440 discloses a system for measuring one or a plurality of regions of an object to be able to determine one or a plurality of dimensions of the object. In one example, the system utilises a mirror arrangement for transmitting pulsed laser light so that the light impinges downwards upon the object and for receiving the upwardly reflected light. The system includes a laser, a rotating planar mirror and a concave frusto-conical mirror encircling the planar mirror, which serve for directing the light beam towards the object. The frusto-conical mirror, the planar mirror and a light receiver serve for receiving light beams which are reflected from the object. Electronic circuitry connected to the light receiver serves for calculating the travel time of the beam to and from the object, with a modulator causing the light beam to be modulated with a fixed frequency and the rotating planar mirror and the frusto-conical mirror causing the light beam to sweep across the object at a defined angle/defined angles relative to a fixed plane of reference during the entire sweeping operation.

EP-A-0747665 describes detection of leading and trailing edges of objects advancing along a defined path. A light source directs a light beam toward a beamspot on the path. Light reflected from the beamspot is received by two light detectors. A leading edge of an advancing object approaching the beamspot substantially blocks the light from being received from one detector and, subsequently, a trailing edge of the object departing from the beamspot substantially blocks the light from being received by the other detector. Electrical circuitry is provided for distinguishing the changes in reflected light received at each detector and determining whether the leading edge or the trailing edge is blocking the reflected light. The data obtained are processed to provide information about the object, such as the height of the leading and trailing edges of the object and the length of the object.

JP-A-61-82106 discloses as conventional a method of detecting unevenness of a road surface from a slowly moving detection vehicle. The vehicle carries a vertically downwardly directed camera for capturing the road surface image and a projector shining light obliquely onto the road surface directly beneath the camera. It describes as its own invention having, instead of the single projector, a pair of projectors at respectively the left- and right-hand sides of the vehicle. The two projectors shine differently coloured light onto the road surface directly under the camera and the illuminated road surface is captured on camera in colour either continuously or at regular intervals. This facilitates distinguishing unevenness of the road surface from cracks therein.

U.S. Pat. No. 5,220,450 discloses a scanning optical system including a gas laser for emitting a writing beam, a rotary polygonal mirror for deflecting and reflecting the rays of light from the gas laser, a scanning lens that is telecentric with respect to an image plane and which focuses the deflected rays of light to form an image on the plane, a focus detector that receives the reflected light from the image plane to detect the state of focusing on the plane by the scanning lens, and a focus adjusting unit that brings the scanning lens into focus on the image plane on the basis of the output of the focus detector.

BRIEF SUMMARY OF THE INVENTION

According to a first aspect of the present invention, there is provided apparatus for automatically inspecting matter, comprising emitting means serving to emit a detection medium, which comprises electromagnetic radiation, to be active at said matter, receiving means in the form of a rotary polygonal mirror arranged to receive from a multiplicity of detection zones at said matter detection medium which has been varied by variations in said matter, detecting means serving to receive the varied medium by reflection from the mirror, to detect a plurality of wavelengths of said varied medium substantially simultaneously, and to generate detection data in respect of said plurality of wavelengths substantially simultaneously and in dependence upon the variations in said medium, and data-obtaining means connected to said detecting means and serving to obtain said detection data therefrom, the arrangement being such that the beams of the varied medium which are received at said detecting means and emanate from the respective detection zones travel along respective paths from said matter to said mirror which paths converge continuously with respect to each other from said matter to said mirror.

According to a second aspect of the present invention, there is provided a method of automatically inspecting matter, comprising emitting from emitting means a detection medium, which comprises electromagnetic radiation, to be active at said matter, said medium being varied by variations in said matter, receiving the varied medium from a multiplicity of detection zones at said matter at receiving means in the form of a rotary polygonal mirror, reflecting the varied medium from the mirror to detecting means, detecting at said detecting means a plurality of wavelengths of said varied medium substantially simultaneously, and generating detection data from said detecting means in respect of said plurality of wavelengths substantially simultaneously and in dependence upon the variations in said medium, the beams of the varied medium which are received at said detecting means and emanate from the respective detection zones travelling along respective paths from said matter to said mirror which paths converge continuously with respect to each other from said matter to said mirror.

According to a third aspect of the present invention, there is provided apparatus for automatically inspecting matter, comprising emitting means serving to emit a detection medium, which comprises electromagnetic radiation, to be active at said matter, a rotary polygonal mirror arranged to receive directly from said matter detection medium varied by variations in said matter, detecting means serving to receive the varied medium by reflection from the rotary polygonal mirror, to detect a plurality of wavelengths of said varied medium substantially simultaneously, and to generate detection data in respect of said plurality of wavelengths substantially simultaneously and in dependence upon the variations in said medium, and data-obtaining means connected to said detecting means and serving to obtain said detection data therefrom.

According to a fourth aspect of the present invention, there is provided apparatus for automatically inspecting matter, comprising emitting means serving to emit a detection medium, which comprises electromagnetic radiation, to be active at said matter, a rotary polygonal mirror arranged to receive from a multiplicity of detection zones at said matter detection medium varied by variations in said matter, at least one folding mirror by way of which said rotary polygonal mirror receives the varied medium, detecting means serving to receive the varied medium by reflection from the rotary polygonal mirror, to detect a plurality of wavelengths of said varied medium substantially simultaneously, and to generate detection data in respect of said plurality of wavelengths substantially simultaneously and in dependence upon the variations in said medium, and data-obtaining means connected to said detecting means and serving to obtain said detection data therefrom, the or each folding mirror being arranged to reflect varied medium from at least some of said multiplicity of detection zones.

Owing to these four aspects of the present invention, it is possible to simplify and thus reduce the cost of the apparatus compared with a known apparatus in which the varied medium is received at the rotary polygonal mirror by way of a mirror of a character which is complicated and expensive to produce.

Preferably, the matter is advanced through a detection station at which the detection medium is active.

The reflective faces of the rotary polygonal mirror are at least two in number and may be either planar or curved and either substantially parallel or inclined to the axis of rotation of the mirror, i.e. the mirror may be cylindrical or pyramidal.

A particular advantage of the feature that the beams of the varied medium travel along paths which converge continuously with respect to each other is that the matter width covered by the rotary polygonal mirror can be changed by changing the spacing between the matter and that mirror, whereby a plurality of arrangements each comprising such rotary polygonal mirror, such detecting means and such data-obtaining means can be disposed side-by-side, particularly in the form of modules, transversely of the matter so that each arrangement inspects part of the width of the matter and the width parts inspected by the respective arrangements overlap each other to desired extents.

According to a fifth aspect of the present invention, there is provided a method of automatically inspecting matter comprised of differing materials, comprising emitting a beam of detection medium so that said beam scans said matter, said medium being varied by variations in the composition of said matter, receiving the varied medium at detecting means, generating detection data from said detecting means in dependence upon the variations in said medium, and identifying at least one of said materials from said data.

According to a sixth aspect of the present invention, there is provided apparatus for automatically inspecting matter comprised of differing materials, comprising emitting means serving to emit a scanning beam of detection medium to scan said matter, receiving means arranged to receive detection medium varied by variations in the composition of said matter, detecting means serving to generate detection data in dependence upon the variations in said medium, and data-obtaining means connected to said detecting means and serving to obtain said detection data therefrom and to identify at least one of said materials from said data.

Owing to these two aspects of the invention, it is possible to save energy in production of the detection medium, without losing intensity level of the varied medium received at the receiving means. If the sensitivity of the detecting means is liable to be saturated by the intensity of the direct return beam, then the detecting means is offset relative to the direct return path. The emitted beam may be continuous or pulsed. It is advantageous to emit two or more scanning beams simultaneously and to direct them at substantially a common region of the station, in order to give widespread exposure to the medium of surface portions of the matter at the region.

Preferably, the matter is advanced through a detection station at which the detection medium is active.

According to a seventh aspect of the present invention, there is provided a method of automatically inspecting matter for varying composition, comprising advancing a stream of said matter comprised of individual objects, emitting a detection medium to be active at a multiplicity of individual detection zones distributed across substantially the width of said stream at a transverse section of said stream, said medium being varied by variations in the composition of said matter at said transverse section, receiving the varied medium at receiving means, generating detection data in dependence upon the variations in said medium, utilising a camera, which is other than said receiving means, to detect spatial characteristics of said objects, and generating further data in dependence upon said spatial characteristics.

According to an eighth aspect of the present invention, there is provided apparatus for automatically inspecting matter for varying composition, comprising detection station means through which a stream of said matter comprised of individual objects advances, emitting means serving to emit a detection medium to be active at a multiplicity of individual detection zones distributed across substantially the width of said stream at a transverse section of said stream at said station means, receiving means serving to receive detection medium varied by variations in the composition of said matter at said section, detecting means serving to generate a first series of detection data in dependence upon the variations in said medium, a camera, which is other than said receiving means, at said station means and serving to detect spatial characteristics of said objects and serving to generate a second series of detection data in dependence upon said spatial characteristics, and data-obtaining means connected to said detecting means and to said camera and serving to obtain the first and second series of detection data therefrom.

The spatial characteristics may comprise profiles of the respective objects or relative positions of the objects.

Owing to these two aspects of the invention, it is possible simply and inexpensively to sort objects according to their size and/or their composition, as desired, and/or to eject at consecutive stages respective fractions of the stream which differ from each other in respect of their characteristics, e.g. their compositions or their colours.

According to a ninth aspect of the present invention, there is provided a method of automatically inspecting matter comprised of differing materials, comprising emitting a detection medium to be active at said matter, said medium being varied by variations in the composition of said matter, receiving the varied medium at receiving means from, in turn, groups of detection spots at said matter, whereof each group contains a plurality of said detection spots and provides one of said detection zones, with the varied medium from all of the detection spots in each group being received substantially simultaneously, generating detection data for each detection zone in dependence upon the variations in said medium at the detection zone, and identifying at least one of said materials from said data.

According to a tenth aspect of the present invention, there is provided apparatus for automatically inspecting matter comprised of differing materials, comprising emitting means serving to emit a detection medium to be active at said matter, receiving means serving to receive detection medium varied by variations in the composition of said matter from, in turn, groups of detection spots at said matter, whereof each group contains a plurality of said detection spots and provides one of said detection zones, with the varied medium from all of the detection spots in each group being received substantially simultaneously, detecting means serving to generate detection data in dependence upon the variations in said medium at each detection zone, and data-obtaining means connected to said detecting means and serving to obtain said detection data therefrom, and to identify at least one of said materials from said data.

Owing to these two aspects of the invention, it is possible to increase the resolution of detection by a factor of the number of detection spots in each zone and thereby to increase the resolution for the same speed of detection, or for a given resolution to increase the speed of detection, without increasing the speed of, for example, a rotary polygonal mirror if provided. Thus, relatively smaller objects can be more accurately identified as to their position (and composition, if desired) so that it is possible to provide a system particularly suited to sorting of granulates.

According to an eleventh aspect of the present invention, there is provided apparatus for automatically inspecting a stream of matter, comprising emitting means serving to emit a detection medium to be active at said matter, first and second receiving means of respective first and second inspection arrangements separate from each other and arranged to receive from said matter detection medium varied by variations in said matter, first and second detecting means of said respective first and second inspection arrangements serving to receive the varied medium by reflection from the receiving means, and to generate detection data in dependence upon the variations in said medium, and data-obtaining means connected to said first and second detecting means and serving to obtain said detection data therefrom.

Owing to this aspect of the invention it is possible to increase the matter width capable of being inspected and/or to improve the resolution of the inspection of the same matter width, in that the inspection arrangements may inspect respective parts of the width of the matter or may each inspect substantially the whole width of the matter. Advantageously, the inspection path of each arrangement is substantially rectilinear and substantially perpendicularly transverse to the matter and, very preferably, the inspection paths are substantially co-incident where they overlap or are directly end-to-end if they do not overlap. It is especially desirable that the inspection arrangements should either commence respective widthwise scans from a common location or terminate respective widthwise scans at a common location. The inspection arrangements may take the form of respective modules arranged side-by-side with each other.

According to a twelfth aspect of the present invention, there is provided a method of automatically inspecting matter, comprising emitting a detection medium, which comprises radiation, as a scanning beam to irradiate a path over said matter, inspecting the irradiated path at an oblique angle to said matter, and ascertaining from that inspection the general profile of that path.

According to a thirteenth aspect of the present invention, there is provided apparatus for automatically inspecting matter, comprising emitting means serving to emit a detection medium, which comprises radiation, as a scanning beam to irradiate a path over said matter, inspecting means arranged to inspect the irradiated path at an oblique angle to said matter, and ascertaining means arranged to ascertain from that inspection the general profile of that path.

Owing to these two aspects of the present invention, it is possible, in a simple manner and with relatively low energy consumption, to ascertain the general profile of the matter, especially the general profiles of objects of which the matter is comprised.

According to a fourteenth aspect of the present invention, there is provided a method of inspecting matter, comprising emitting from emitting means a detection medium, which comprises radiation, to be active at said matter, said medium being varied by variations in said matter, at least part of the emitted medium passing through said matter and the varied medium which has passed through said matter being received at detecting means, and preventing said detecting means from receiving the medium directly from the emitting means.

According to an fifteenth aspect of the present invention, there is provided apparatus for inspecting matter, comprising emitting means serving to emit a detection medium, which comprises radiation, to be active at said matter, detecting means arranged to receive, by passage of the medium through said matter, detection medium varied by variations in said matter, and shielding means arranged to prevent the detecting means from receiving the medium directly from the emitting means.

Owing to these aspects of the invention it is possible to prevent swamping of the detecting means by medium received directly from the emitting means, and thus for the receiving means to be relatively highly sensitive to variations in the medium.

According to a sixteenth aspect of the present invention, there is provided apparatus for inspecting matter, comprising emitting means serving to emit a detection medium, which comprises radiation, to be active at said matter, detecting means arranged to receive, by passage of the medium through said matter, detection medium varied by variations in said matter, and receiving means located between said emitting means and said detecting means and through which the varied medium is arranged to pass, said receiving means comprising a Fresnel lens.

Owing to this aspect of the invention, the radiation can pass in a parallel manner through the matter, so that the matter is more uniformly irradiated than if the radiation were to pass in a converging manner therethrough.

The present invention is applicable to a wide variety of systems of automatically inspecting matter.

By applying multiple sensors and/or a scanning arrangement, it becomes possible to introduce a large number of detection points.

The detection medium can be electromagnetic radiation, for example IR or visible light, to detect variations in constituency or colour, or an electromagnetic field to detect metal portions of the stream, e.g. in sorting of materials. A wide variety of materials may be sorted from each other, but particularly plastics-surfaced objects sorted from other objects. For the present automatic sorting, the objects must be distributed in substantially a single layer.

By using visible light as the detection medium and performing analysis of a plurality of wavelengths in the visible light spectrum substantially simultaneously with each other upon the varied medium, it is possible to identify colour of the matter more accurately, which is particularly advantageous when sorting slightly coloured containers, for example.

If the matter advances at the detection station in a freely falling condition, it is possible to carry out the detection without needing to take into account the presence of some conveying means and also possible to carry out reflection-reliant detection at a substantially constant spacing between the advancing matter and the receiving means. Moreover, the feature whereby the matter falls more vertically than horizontally (preferably either vertically or almost vertically) at the detection level has the advantage that the apparatus can be compact horizontally, which is a particularly desired feature in a recycling plant. By means of a suitable deflector above the level at which the detection medium is to be active, the matter can be caused to fall freely in a curved distribution around a vertical axis, most preferably at a substantially constant radius from that axis.

By providing first and second receivers to receive, in respective different directions inclined to each other and from a common zone of matter, detection medium varied by variations in the matter, first and second detecting means arranged to scan the matter transversely of a feed direction of the matter while generating first and second series of detection data in dependence upon the variations in the medium received at the first and second receivers, and data-obtaining means connected to the first and second detecting means and serving to obtain the first and second series of detection data therefrom and to use the first and second series of detection data to obtain an indication of the height of said common zone, it is possible to identify uncrushed containers, for example, in the matter, since, if, say, the intensity of the medium is varied by variations in the orientation of the matter at respective detection zones at the matter, then the volume of the containers can be determined by the comparison of the first and second series of data. Furthermore, if, say, the wavelength of the medium is varied by variations in the composition of the matter at those detection zones, then also the composition of the containers can be determined.

By scanning an object transversely of its feed direction and receiving detection medium varied in its intensity in dependence upon the respective orientations of differently orientated surfaces of the object it is possible to identify an uncrushed container, for example, since irradiation from one general direction will produce variations in the intensity of the irradiation of the surfaces in dependence upon their orientation and from the consequential variations in the reflected medium the volume of the container can be determined. Furthermore, if, say, the wavelength of the medium is varied by variations in the composition of the containers, then also the composition of the containers can be determined.

For sorting of objects, the objects may be caused to fall freely. Alternatively, they may be advanced through the detection station on an endless conveyor belt. If the objects to be separated-out are plastics objects which are substantially transparent to the electromagnetic radiation, e.g. IR, then the conveying surface of the belt should be diffusely reflective of the electromagnetic radiation.

For a polymer, two or more detection wavelength bands in the NIR region of 1.5 microns to 1.85 microns can be employed. For a laminate comprised of polyethylene on paperboard, a first wavelength band centred on substantially 1.73 microns is employed, as well as a second wavelength band centred less than 0.1 microns from the first band, for example at about 1.66 microns.

The matter may comprise laminate comprised of a first layer and a second layer underneath said first layer and of a material having a spectrum of reflected substantially invisible electromagnetic radiation significantly different from that of the material of the first layer. As a result, the spectrum of substantially invisible electromagnetic radiation, particularly IR, reflected from such laminate can be readily distinguishably different from the spectrum of that radiation reflected from a single layer of the material of either of its layers.

If the stream is a continuous strip of laminate advancing on a laminating machine, for example a polymer coating machine coating a polymer layer onto a substrate, it is possible to detect any variation in composition of the advancing polymer layer and to correct the coating process accordingly.

Alternatively, it is possible to separate-out objects, e.g. waste objects, of a predetermined composition from a stream of matter, e.g. waste matter, which can be relatively wide compared with a sequential stream, so that a relatively high rate of separation can be achieved.

Typically, there could be a transverse row of some 25 to 50 detection zones for a stream 1 m. wide. A central detection system can be applied to "serve" all 25 to 50 detection zones if there is sufficient IR intensity across the width of the stream from a single or multiple IR source or even if there is an infrared source at each detection point. Optical fibres may lead the reflected IR from the detection points to this central detection system. However, a system of IR reflectors is preferred to optical fibres, since a reflector system is less expensive, allows operation at higher IR intensity levels (since it involves lower IR signal losses) and is less demanding of well-defined focal depths. If the stream moves at some 2.5 m/sec. and the system is capable of 100 to 160 scans across the stream each second, then detections can be made at a spacing of some 2.5 to 1.5 cm along the stream. When each scan is divided into 25 to 50 detection zones, detections can be made in a grid of from 1.5×2.0 cm. to 2.5×4.0 cm. The transverse scanning of the moving stream makes it possible to construct a two-dimensional simulation which can be analysed using image processing. In this way it is possible to detect:

matter composition, e.g. thickness, and position in the stream shape and size of composition variation several composition variations substantially simultaneously.

The detection data processing system will determine wanted/unwanted composition at each detection zone.

For food quality control, e.g. fat content and maturing of fish and the maturing of meat, the apparatus measures the quality of foodstuff by monitoring the absorption spectrum in the IR range.

Although an advantage of arranging the detection of objects from underneath (rather than above) the waste stream is that it gives as uniform a distance from detection point to object as possible, it has disadvantages. By irradiating the waste objects on a conveyor belt with radiation from above and by utilising a reflector system to select that portion of the reflected radiation which propagates upwards, the system can be made very focusing insensitive. The alternative of the stream being in free fall is particularly advantageous in enabling the distance from detection point to object to be as uniform as possible, while avoiding many of the disadvantages of detection from underneath.

In addition to or instead of spectral sensing devices, electromagnetic sensing devices may be employed at a metal-detection station. By means of an antenna extending across the advancing stream, an alternating electromagnetic field can be set up across the stream. By providing as many eddy current detection zones (in the form of individual detection coils) across the stream as there are spectral detection zones a simultaneous metal detection can be performed at very low additional cost. Thereby, with a waste stream including polymer-coated beverage cartons, and with several air jet arrays arranged one after another it becomes possible to sort out:

beverage cartons without an aluminium barrier beverage cartons with an aluminium barrier other metal-containing objects.

With a more elaborate spectral analysis it also becomes possible to identify and sort out the type of polymer in a plastics object. The system could hence be applied to sorting into separate fractions the various plastics types occurring.

By employing one-and-the-same detection station for at least two streams simultaneously, the cost of inspection can be reduced compared with a case where the streams have respective detection stations.

BRIEF DESCRIPTION OF THE DRAWINGS

In order that the invention may be clearly and completely disclosed, reference will now be made, by way of example, to the accompanying drawings, in which:—

DETAILED DESCRIPTION OF THE PREFERRED EMBODIMENTS OF THE INVENTION

The present system utilises principles of the system of WO-A-96/06689 and reference should be made to the latter for any necessary clarification of the present description with reference to the present drawings.

Figure 1:
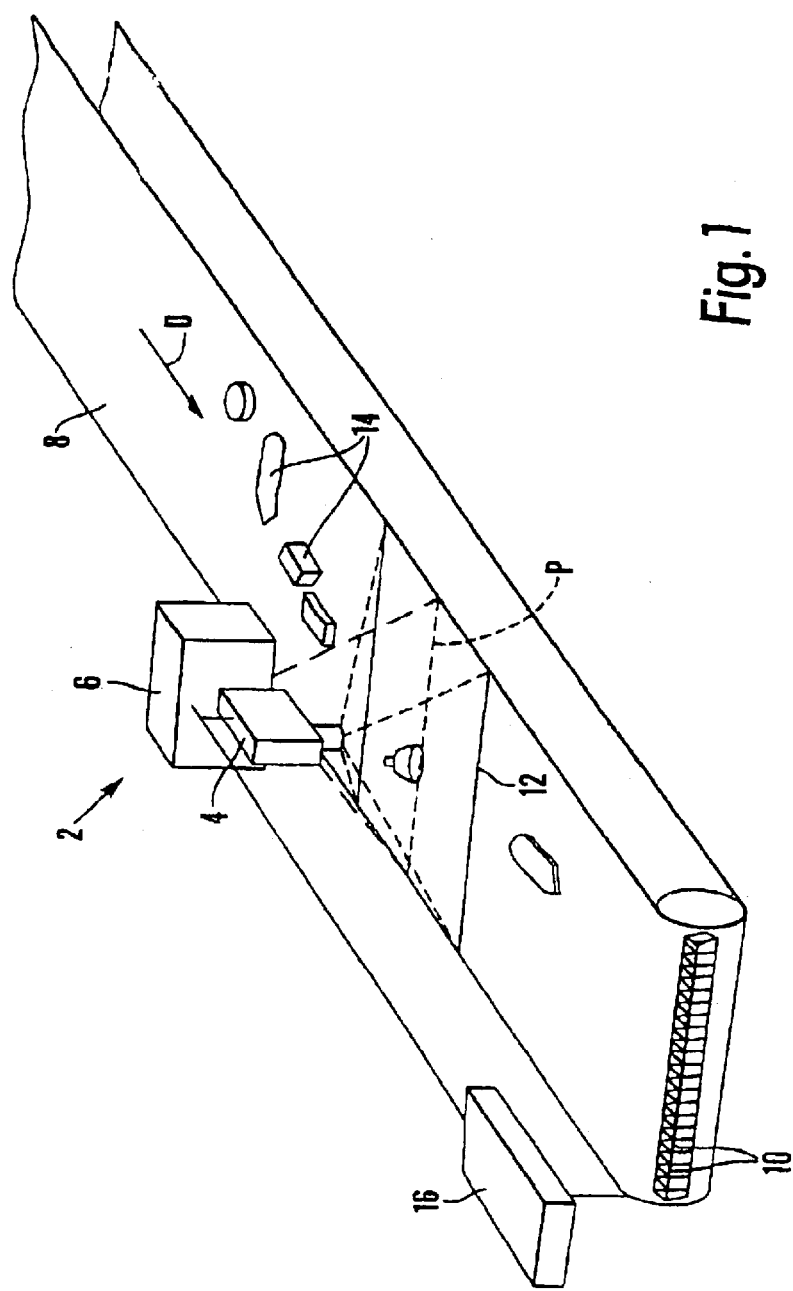
FIG. 1 illustrates diagrammatically, in perspective view from above, a system for automatic sorting of waste objects of differing compositions.

Referring to FIG. 1, a detection station 2 including a vertically downwardly directed video camera 4 and a detection unit 6 identical to one of the two units 6 to be described with reference to FIGS. 2 and 3 has a stream of waste matter, including objects 14 such as containers, advanced therethrough on a substantially horizontal conveyor belt 8 to a transverse array of air jet nozzles 10. The rectangular picture area of the camera is indicated at 12 and spans the whole width of the belt 8 and thus of the stream of waste. The data from the camera 4 is used to identify the positions of individual objects in the waste stream (in the sense of approximately the region that the object occupies in the stream of waste). The unit 6 scans the stream of waste along a rectilinear path P also extending the whole width of the belt 8 and thus of the waste stream, the path P being perpendicular to the longitudinal direction D of the belt 8, i.e. to the feed direction of the waste stream. By infrared spectrum analysis, the unit 6 detects the composition of at least some of the objects 14 in the waste stream. The data from the camera 4 and the unit 6 are used to control a controller 16 for solenoid valves (not shown) which control the supply of compressed air to the respective nozzles 10. In this relatively simple system, the composition and/or colour of each object is/are detected by the unit 6, whilst the video camera is used to monitor the scanned region and its data output employed automatically to detect the positions of the objects and to correct the data relating to those objects as received from detectors 21 in the unit 6. The belt 8 may be 0.5 m. wide and the camera 4 and the unit 6 be active over the whole width of the belt.

Figure 2:
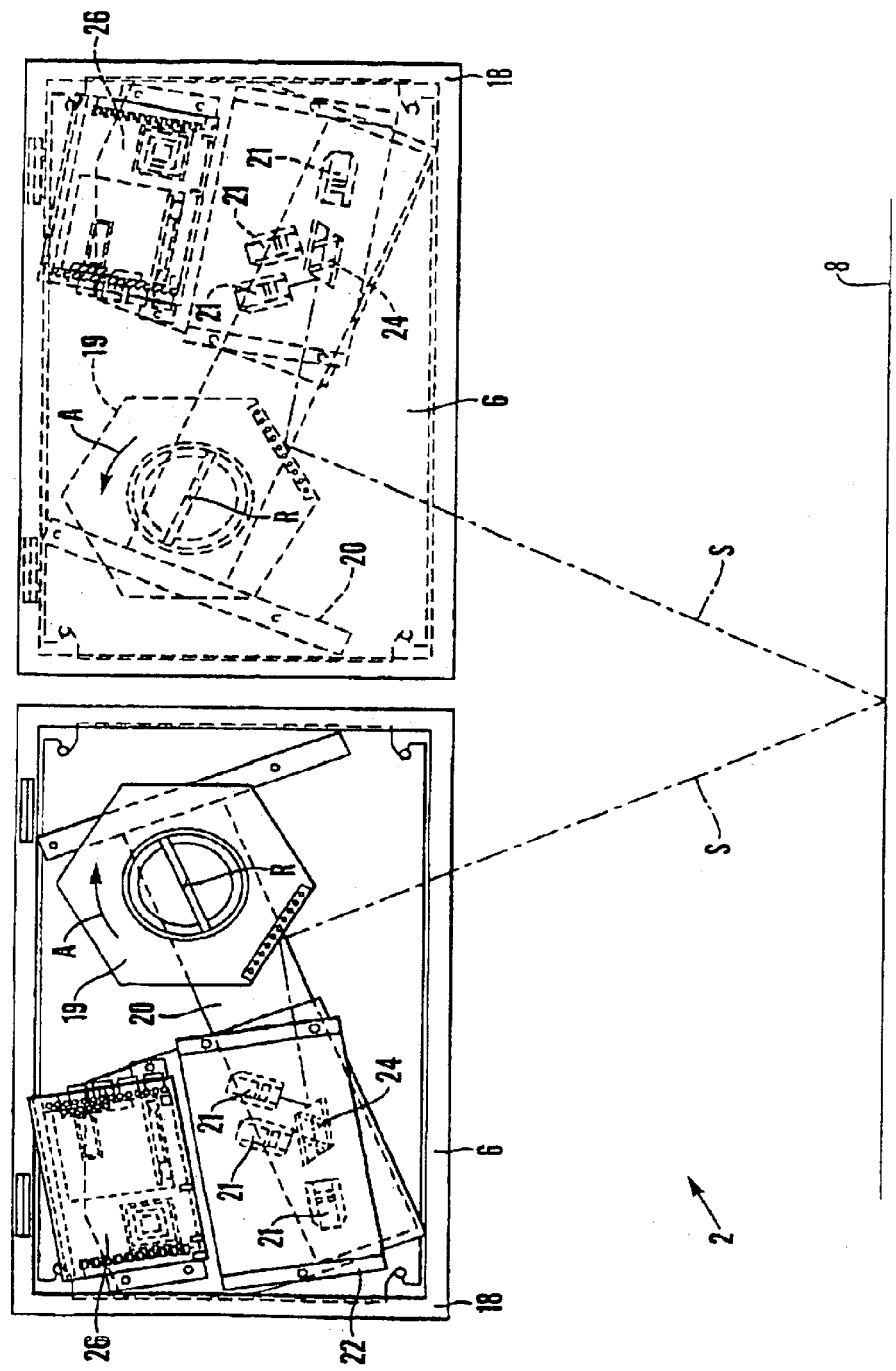
FIG. 2 illustrates diagrammatically, in front elevation, a modified version of the system, with two rotary polygonal mirrors in respective first angular positions.
Figure 3:
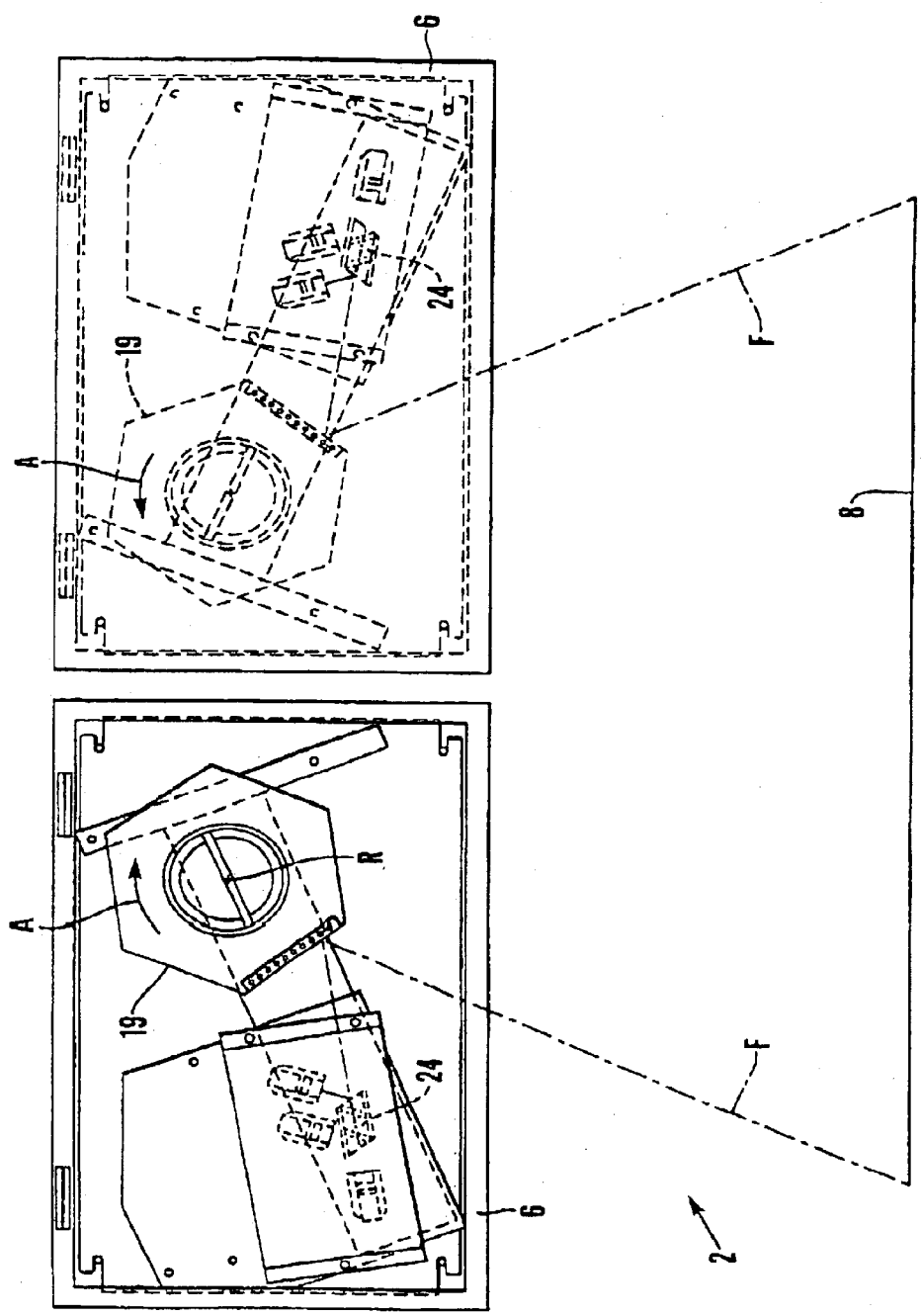
FIG. 3 is a view similar to FIG. 2, but with the mirrors in second angular positions.

Referring to FIGS. 2 and 3, the units 6 are arranged side-by-side above the conveyor belt 8 which, in this version, may be 1.0 m. wide. Each unit includes a housing 18, of which the front cover has been removed from the left-hand unit in FIGS. 2 and 3. Each housing 18 contains a mounting bracket 20. The detection station 2 differs from the detection station 131 of the version of FIG. 11 of WO-A-96/06689 chiefly in that there are two units 6 disposed side-by-side and that, in each unit 6, the cylindrical, polygonal mirror 108 of that FIG. 11 has been re-orientated such that its axis of rotation R now extends in the feed direction D (such mirror being referenced 19 in the present drawings). Not only does this change simplify the path of transmission of the varied IR radiation from the stream of matter to the filter/detector combinations 21, but the loss of IR intensity produced by such a relatively long path as in that FIG. 11 can be minimised. The filters/detectors 21 are parts of an optical detection device 22 which includes a beam splitter 24 and is mounted on the bracket 20. Also mounted on the bracket 20 is a microprocessor 26 which receives the data output from the filter/detectors 21 (and from the camera 4 if provided) and data as to the angular position of the rotating polygonal mirror 19 and controls accordingly the controller 16. The polygonal mirrors 19 rotate in the senses of the arrows A and the starting path of the diffusely reflected IR via each mirror 19 to its associated beam splitter 24 at the commencement of a scan is indicated by the dot-dash line S and its finishing path at the end of the scan is indicated by the dot-dash line P. Although not illustrated, the beams of the varied detection medium which are received at each detection device 22 and emanate from the respective detection zones at the waste stream travel along respective paths from the waste stream to the associated mirror 19 which paths converge continuously with respect to each other from the waste stream to that mirror. One unit 6, or a row of at least two units 6 side-by-side, is/are applicable not only to material being advanced by a conveyor belt, but also to material advancing down a slide or to material advancing in free fall. With the three filter/detectors 21 shown, the unit 6 is able to perform simultaneous analysis of three wavelengths of electromagnetic radiation. At least three wavelengths and thus a corresponding number of filter/detectors are chosen if IR is used as the detection medium, in order to detect composition of the matter, or at least two wavelengths and thus at least two filter/detectors in the event that visible light is chosen as the detection medium, in order to determine the colour of the matter. The polygonal mirror gives relatively high scanning speed with relatively moderate rotational speed of the mirror. The radiation reflected from the matter over the scanning width is converging.

The spacing between the or each polygonal mirror and the stream of matter is kept as small as practical, in order to maintain high resolution and intensity of reflected radiation with relatively low illumination intensity.

Figure 11:
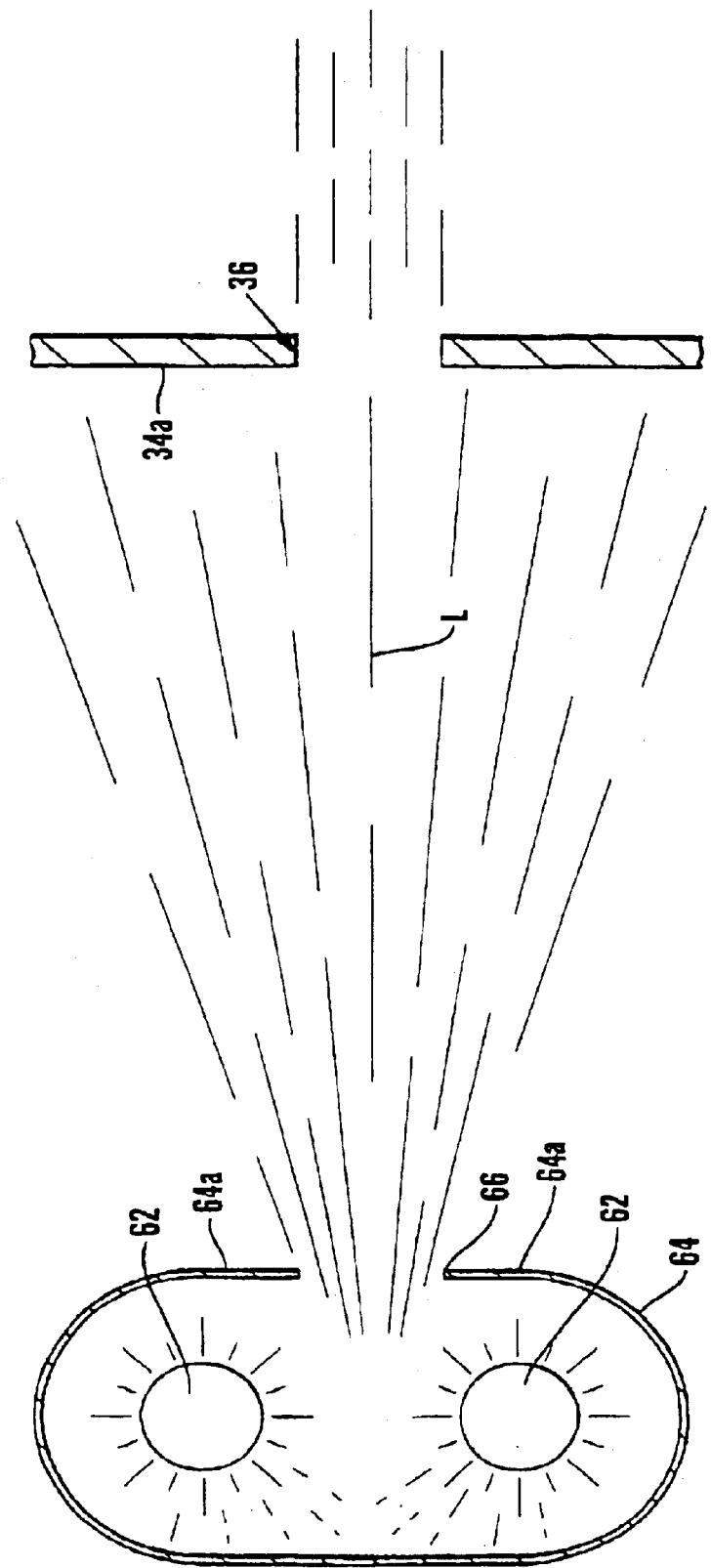
FIG. 11 shows a detail of FIG. 9.

Compared with, for example, the detection system of FIG. 11 of WO-A-96/06689, the system of the present FIGS. 2 and 3 allows a higher resolution and a somewhat better signal-to-noise ratio to be obtained. Moreover, the distance which the reflected radiation has to travel from the matter to reach the filter/detectors 21 can be relatively reduced by up to one half, so reducing light transmission losses, which can be quite significant if the reflected radiation has to travel through a polluted, e.g. dusty, atmosphere and/or indirectly via an intermediate mirror.

Parallactic and shadowing effects can be kept within tolerable limits for objects less than, e.g. 200 mm., tall if the transverse angle of reflection can be kept within some 30° from the vertical. During each scan, the reflection point on the polygonal mirror will move over the surface of the mirror in the direction of scan, which somewhat reduces the angle of reflection towards the end of the scan.

With an hexagonal mirror, for example, a new scan will start upon 60° rotation of the mirror. However, each scan requires somewhat less than half of that 60° rotation to be completed, and thus an interval probably longer than the actual scan period exists in which, for instance, some detector calibration can be undertaken. However, the spectral analysis and two-dimensional simulation of the stream are largely carried out in parallel with the data acquisition, which is practically continuous.

An average minimum object height of, for example, 3 cm. may be pre-set as a reference to correct for some of the parallactic error.

It is advantageous to have a slight overlap of the inner ends of the widths scanned by the two units 6, in order to avoid inadvertent failure to detect objects or parts of objects in the border zone. Each unit 6 operates independently of the other, even to the extent of controlling its own array of air jet nozzles (not shown).

Figure 4:
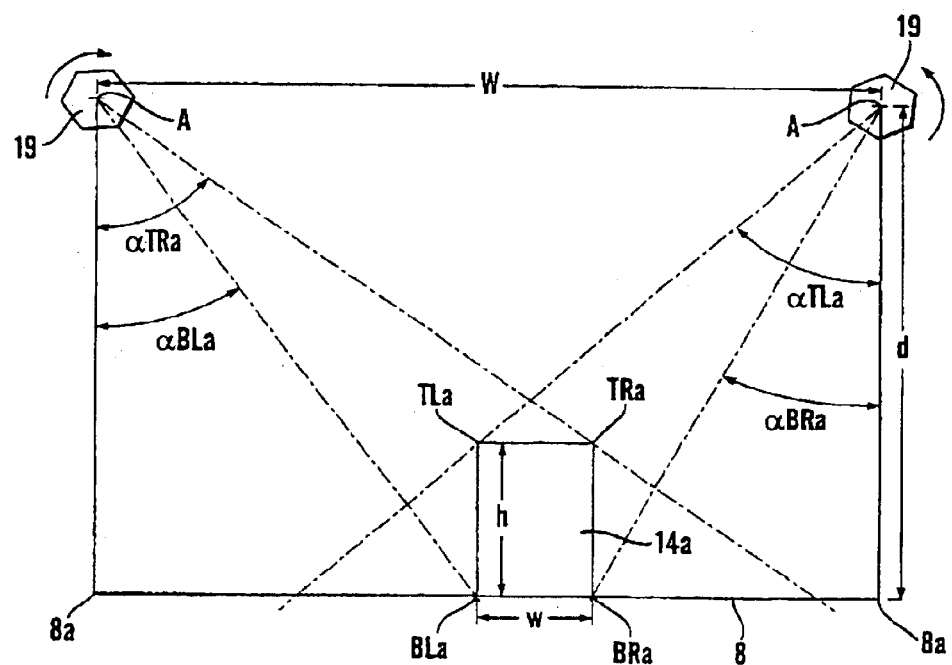
FIG. 4 is a view similar to FIG. 2 or 3, but of another modified version of the system.

In an alternative embodiment the widths scanned by the two mirrors 19 may overlap fully, the mirrors 19 being displaced relatively further from the advancing matter than as shown in FIGS. 2 and 3. If the mirrors 19 are placed substantially directly above the respective edges of the stream of matter as shown in FIG. 4, the parallactic and shadowing effects can be cancelled out during the processing of the data. Naturally, a higher intensity of illumination of the matter will be required.

Referring to FIG. 4, the axes A of the mirrors 19 are directly above and parallel to the respective edges 8a of the belt 8 and are disposed at the same level as each other at a known distance a above the belt 8 which is of a known width W. An object 14a is shown disposed on the belt 8 having top, left-hand corner TLa, top right-hand corner TRa, bottom left-hand corner BLa, and bottom right-hand corner BRa. It will be understood that position (BLa-BRa) relative to the belt, object height h and object width w can be determined once angles $\alpha$ TRa and $\alpha$ BLa relative to the left-hand axis A and $\alpha$ TLa and $\alpha$ BRa relative to the right-hand axis A are known. These angles refer to the points TRa to BRa, respectively, at which sudden variations of wavelength and/or intensity of the diffusely reflected IR received by the left-hand or right-hand mirror take place, so that these angles can be determined by the microprocessor 26 from the detection data received thereby.

If there is, for one of the mirrors 19, a sudden variation of the diffusely reflected IR at the point TLa (for the left-hand mirror 19) or TRa (for the right-hand mirror 19), for example because the top surface (between TRa and TLa) is more intensely irradiated with IR than the side surface (between TLa and BLa or between TRa and BRa), then the other unit 6 can be dispensed with, because the one unit 6 on its own can measure position and both h and w.

In still another embodiment, using one polygonal mirror 19, it is possible to have multiple detectors for each wavelength in the device 22. In this way, either, as will be described with reference to FIG. 7 the optical resolution can be improved, thereby assisting detection of very small objects such as might be present in streams of fragmented matter, or the same optical resolution of a scanning module 6 could be maintained whilst increasing the spacing between the mirror 19 and the matter.

Figure 5:
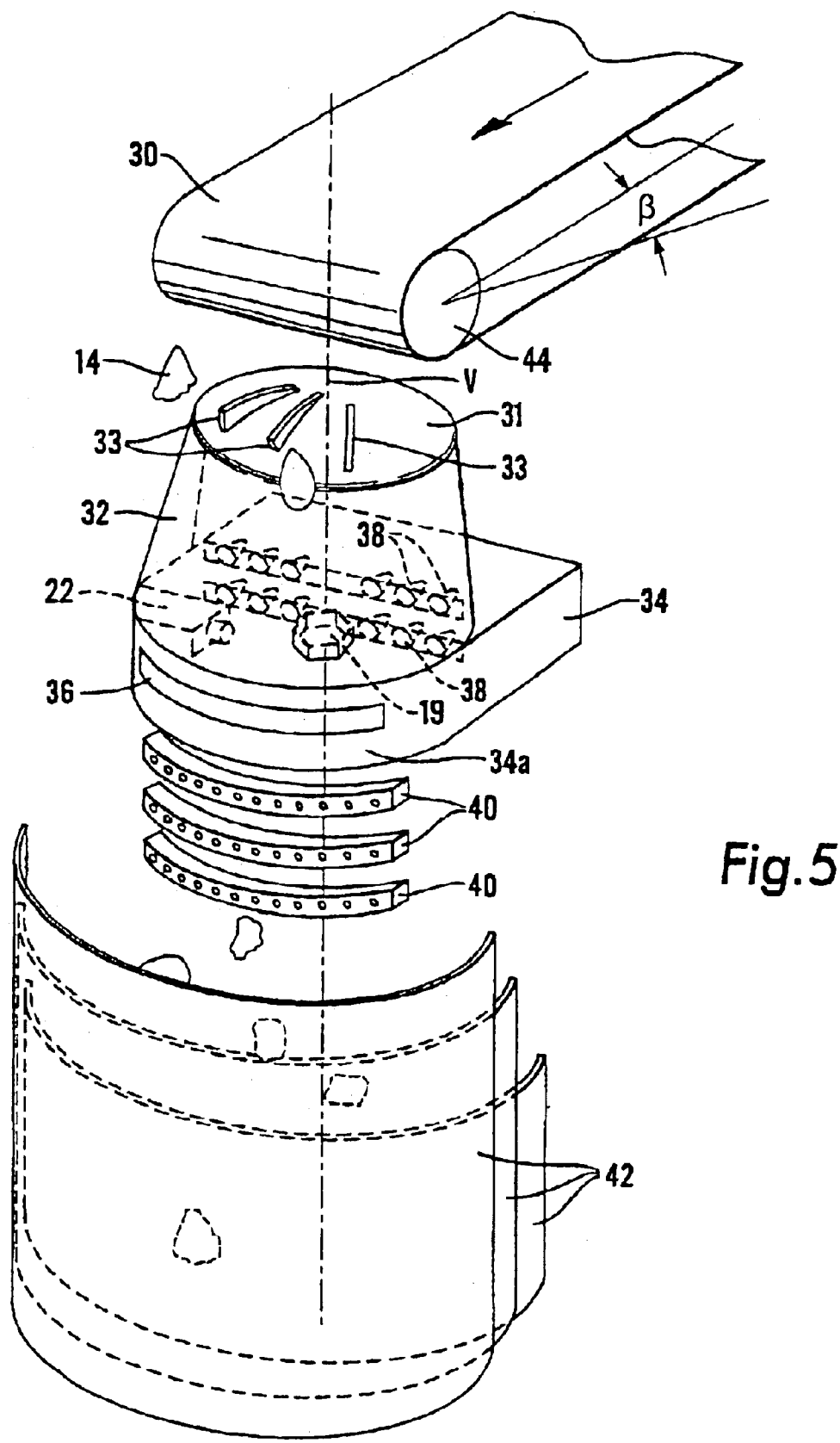
FIG. 5 illustrates diagrammatically, in perspective view from above, a further modified version of the system.

Referring to FIG. 5, waste matter advanced by a feed conveyor belt 30 inclined downwardly at a slight angle β to the vertical drops onto a dome 31 surmounting a conical or elliptical deflector 32 so that the waste becomes distributed at a substantially constant radius about a vertical axis V of the deflector 32. The dome 31 is provided with outwardly diverging guide fins 33 so as to spread the waste matter more evenly around the conical or elliptical deflector 32. A higher sorting capacity can be achieved by the provision of the fins 33, since the tendency for the waste matter to be concentrated at the middle of the front of the circumference of the deflector 32 is reduced, in other words more waste matter can be sorted because the waste matter can be denser in the stream passing over the deflector 32 without portions of the waste matter overlapping each other. Below the deflector is a housing 34 having its front wall 34a substantially coaxial with the axis V and formed with a horizontal slot 36 also co-axial with the axis V and at the same level as a cylindrical, rotary, polygonal mirror 19 co-axial with and rotating about the axis V, and as an optical detection device 22. The housing 34 also contains lamps 38 for illuminating the matter falling freely past the slot 36. Radiation reflected from the falling matter is then reflected to the mirror 19, which scans the falling matter at a substantially constant distance from the matter in the horizontal plane of the slot 36. Arranged below the housing 34 are a number of air jet nozzle arrays 40 arranged parallelly with the slot 36 at substantially the same radius from the axis V. Arranged radially outwardly beyond the falling matter are a number of collector shields 42 spaced radially outwardly from each other. The greater its radius from the axis V, the higher the shield 42 extends.

In use, the composition of the matter falling past the slot 36 and/or the relative position of objects 14 falling past that slot is/are detected and the nozzles of the arrays 40 activated accordingly, to sort the objects 14 into the spaces among the shields 42 and at the outside of the outermost shield 42, the remainder of the matter simply continuing to fall vertically to the inside of the innermost shield 42.

The downward inclination of the belt 30 is provided to promote downward acceleration of the matter as it leaves the belt. This downward acceleration increases vertical speed of the matter and thereby the capacity of the apparatus. It may also be advantageous to have a relatively large radius of the front end roller 44 of the belt conveyor to promote such downward acceleration and to reduce rolling of the objects 14.

Use of the finned dome 31 and the deflector 32 promotes distribution of matter into a freely falling distribution co-axial with the axis V. This has the advantage that, because the mirror 19 is also co-axial with the axis V, no significant parallactic error arises. Instead of the lamps 38 being mounted within the housing 34, they may be mounted exteriorly thereof.

In the version of FIG. 5, the detecting means, the illuminating means and the ejecting means can be assembled as a single unit. It is believed that ejection of more than one fraction of the matter is feasible at different levels as the matter is falling. However, monitoring by camera may be required to give more precise ejection, especially if more than two desired fractions are to be ejected.

The system of FIG. 5 has a particular advantage in that it can occupy less floor area than an equivalent horizontal system.

Figure 6:
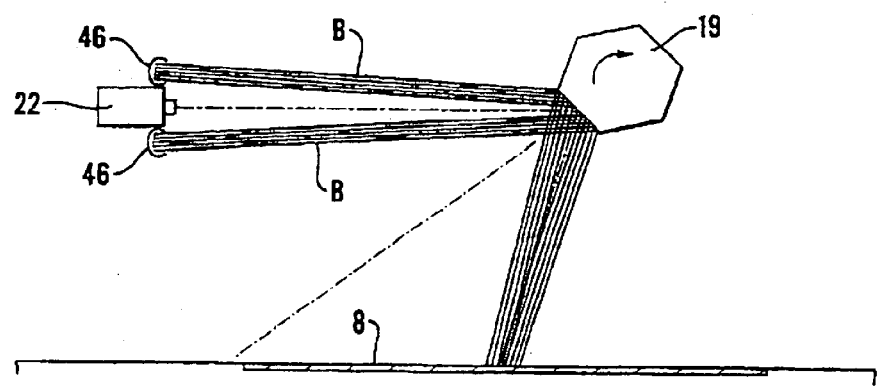
FIG. 6 illustrates diagrammatically, in front elevation, a modification of the system.

Referring to FIG. 6, although this modification is illustrated in relation to matter on a conveyor belt 8, it is also applicable to matter advancing down a slide or to matter in free fall. A polygonal mirror 19 is again shown scanning the matter; however, in this case the mirror 19 is not only receiving reflected light from the matter on the belt 8 and reflecting it to the optical detection device 22, but it is also receiving the matter-illuminating electromagnetic radiation, for example visible light, from two collimators 46 and reflecting the collimated light beams B onto a transversely scanning spot on the matter. This alternative to having stationary light sources has the advantage of greatly reducing the illumination energy requirements for the same reflected radiation intensity level at the device 22. Use of the hexagonal mirror (possibly via another mirror between it and the advancing matter) for reflection of both the illuminating beams and the return beams has the advantage of providing totally reliable synchronisation thereof. Alternatively, it would be possible to use two separate polygonal mirrors, one for the illuminating beams and one for the return beams, on either the same rotary body, or on differing rotary bodies but then, in the latter case, some form of synchronising arrangement would additionally be required. Whatever the light sources used, be they the collimators 46 or otherwise, direct radiation reflection onto the splitters in the device 22 may present the problem of saturating the sensitivity of the detectors, in which case such direct reflection must be avoided. This can be achieved by offsetting the light sources relative to the beam splitters, as indicated in FIG. 6. If desired, the separate collimators 46 could be replaced by a ring-shaped collimator centred around the radiation inlet of the device 22.

Figure 7:
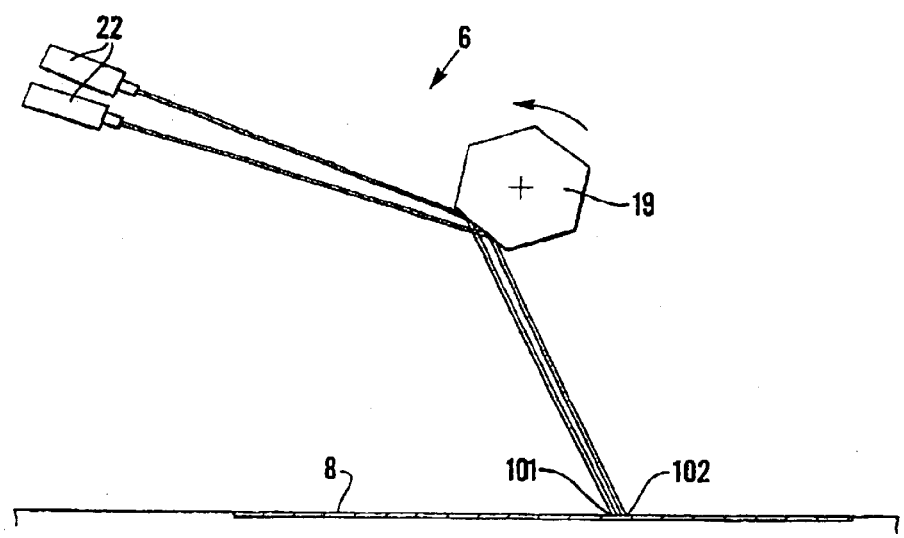
FIG. 7 is a view similar to FIG. 6 of another modification of the system.

In the modification shown in FIG. 7 (again applicable to matter on the belt 8 or advancing down a slide or in free fall), the unit 6 contains, in addition to the mirror 19 and the microprocessor 26 (not shown), two devices 22 side-by-side with each other and arranged to receive diffusely reflected radiation simultaneously from respective detection spots 101 and 102 located adjacent each other along the path P, so that there are there are two filter/detectors 21 (not seen) for the or each electromagnetic radiation wavelength detected. As scanning proceeds, different detection zones, i.e. pairs of detection spots, along the path P are inspected. In a variation (not illustrated) of that modification, the two devices 22 are replaced by a single device 22 containing double filter/detectors 21.

Figure 8:
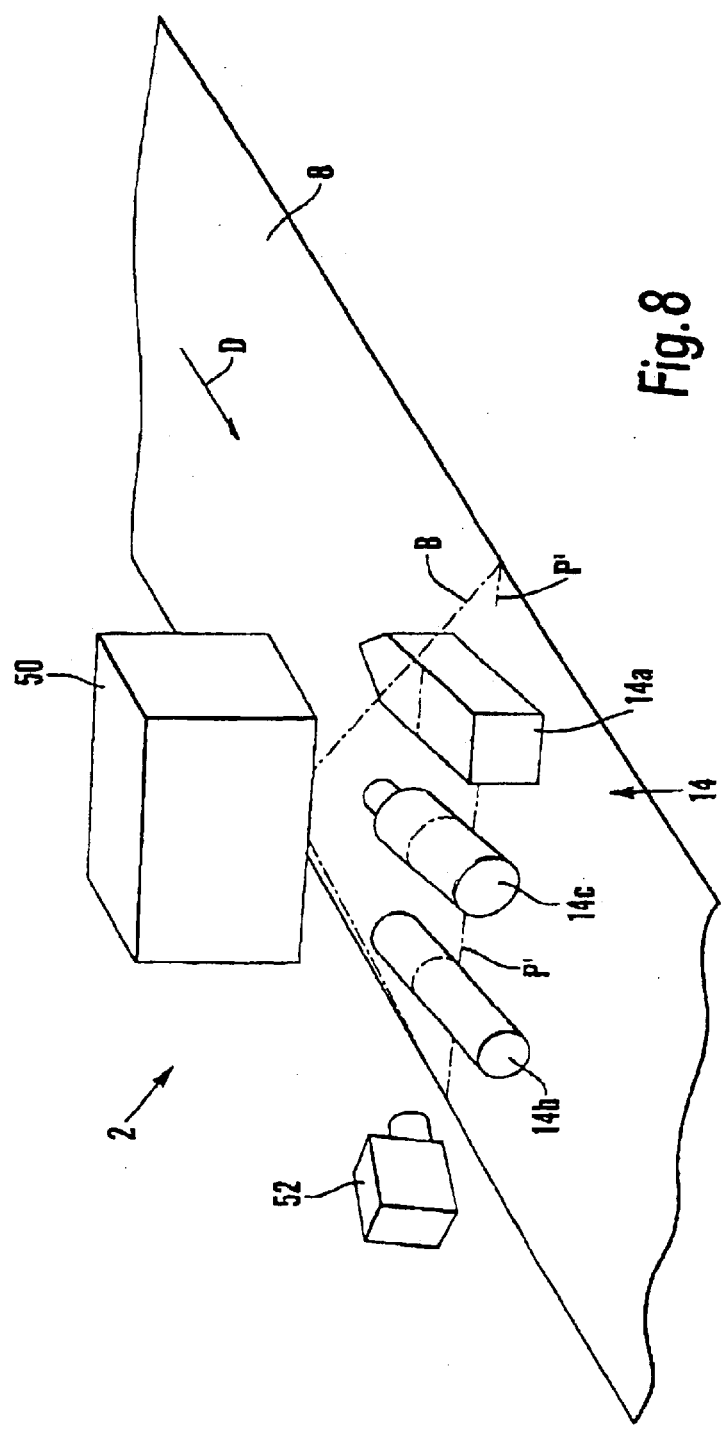
FIG. 8 is a view similar to FIG. 1 of a yet further modified version of the system.

Referring to FIG. 8, in this version a module 50 emits a transversely scanning beam B of electromagnetic radiation visible to a camera 52 directed obliquely to the direction D and disposed in a central vertical plane of the belt 8. The beam B irradiates a path which extends across the belt 8 and generally up, over and down each object 14 being advanced by the belt 8 at the detection station 2. The camera 52 can thereby be employed to detect the general profile of each object, for example as to whether it is of rectangular cross-section, as is the gable-topped carton 14a, of substantially constant circular cross-section, as is the can 14b, or of varying circular cross-section, as is the bottle 14c. The camera 52 also detects the positions of the objects 14. It is thus possible to sort these objects from one another. In addition, if the module 50 has the same capability as does the module 6, with the modification according to FIG. 6, of determining the compositions of the objects 14 from diffusely reflected electromagnetic radiation of the beam B, the compositions of the objects, as well as their general profiles and positions, can be determined. This version is, of course, applicable not only to material being advanced by the belt 8 but also to material advancing down a slide or in free fall.

Figure 9:
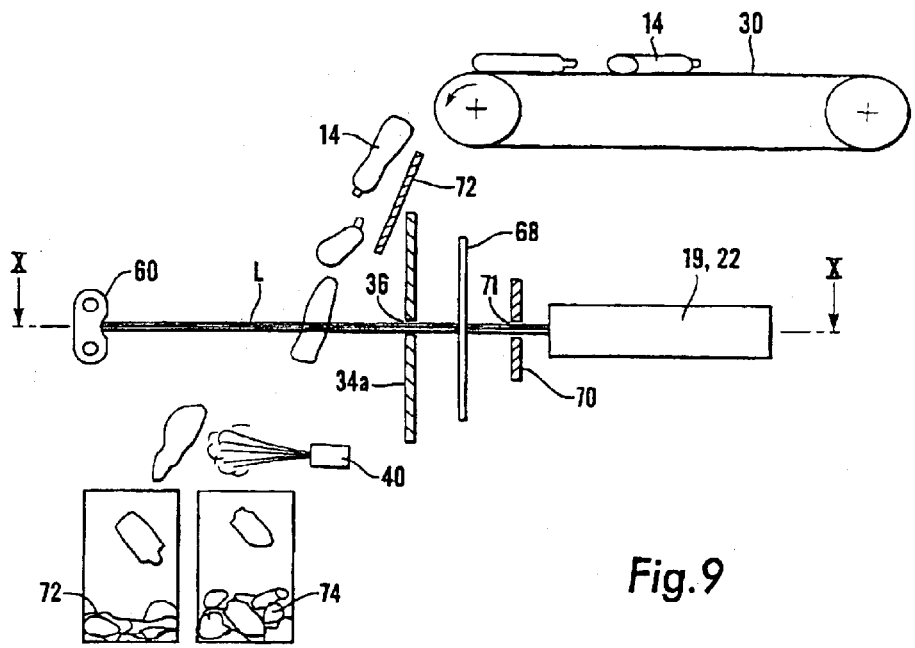
FIG. 9 shows a diagrammatic vertical section through a still further modified version of the system.
Figure 10:
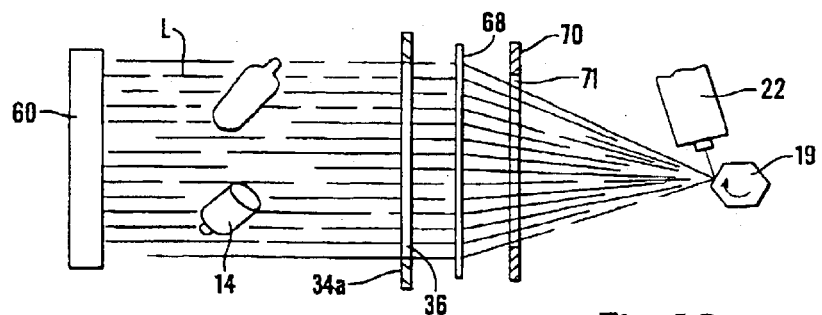
FIG. 10 shows a diagrammatic horizontal section taken on the line X—X of FIG. 9.

Referring to FIGS. 9 to 11 this version differs from that of FIG. 5 chiefly in that the radiation, which comprises visible light L, passes through the matter 14 to be inspected. Thus the light source 60 is disposed outside the housing 34 which contains the rotary polygonal mirror 19 and the detection device 22. The light source 60 contains two horizontal fluorescent tubes 62 which each extend over the whole width of the stream of matter 14 and are surrounded by a horizontal casing 64 except for a horizontal slot-form exit 66 for the light. The tubes 62 are arranged respectively above and below the exit 66, and the internal surface of the casing 64 is reflective of visible light. Thus, the light L leaving the exit 66 has been collimated to some extent. The use of relatively collimated light substantially normal to the stream of matter 14 should facilitate reliable analysis. The light passes through the slot 36 to a Fresnel lens 68 which extends over the width of the stream of matter 14 and, at least in a horizontal plane, causes the light L to converge to an inner wall 70 formed with an inner aperture 71 in the form of a horizontal slot, whence the light L continues to converge towards the polygonal mirror 19. The arrangement is such that the portions 64a of the casing 64 prevent the light L from travelling directly from the fluorescent tubes 62 to the detection device 22. The matter 14 is particularly advantageously in the form of crushed bottles of differing colours of relatively transparent plastics. The bottles leaving the conveyor belt 30 strike a short guide 72 which discourages spinning of the crushed bottles about their own axes; this reduces the production of false data from the device 22. Depending upon the colours of plastics identified from the inspection of the bottles, the air jet nozzle array(s) 40 sort(s) the matter 14 into one or more desired colour fractions 72 and a remaining fraction 74.

In operation, three wavelengths of the radiation, i.e. three colours, are analysed, all in the spectrum (400 to 700 nm) of visible light).

It is believed that, by having at least two fluorescent tubes 62 and by using only diffusely reflected light for penetration of the objects, with mixing of the light from the plurality of tubes 62, reduces the effect of ageing of the tubes 62.

The front wall 34a helps to prevent the matter 14 from fouling the lens 68, whilst the inner wall 70 suppresses stray reflections and multiple images.

It will be noted that the matter 14 in free fall at the detection level in FIGS. 5 and 9 is travelling more vertically than horizontally. This has the advantage that a relatively small floor area can be occupied by the apparatus, which is a feature of particular advantage in recycling plants or on lorries where plenty of vertical space, but not of horizontal space, is usually available. Moreover, this is the preferred arrangement when the apparatus is to eject by means of nozzle arrays 40 a plurality of fractions of the matter 14 on the basis of one scan of the matter.

Figure 12:
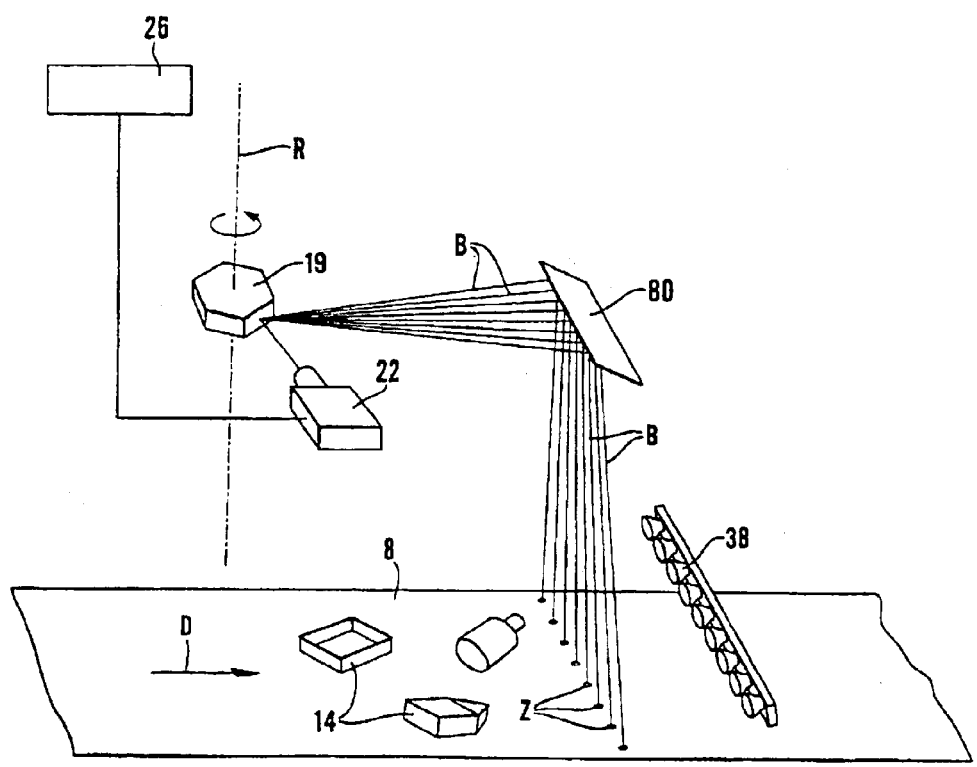
FIG. 12 shows a diagrammatic, fragmentary, perspective view of a yet still further modified version of the system.

In the version shown in FIG. 12, the beams B of the varied detection medium which are received at the detection device 22 and emanate from the respective detection zones Z travel along respective paths from the stream of matter to the rotary polygonal mirror 19 which paths converge continuously with respect to each other from the stream of matter to the mirror 19, although in this case the beams B travel via a planar mirror 80 from the stream of matter to the mirror 19. This version is, of course, applicable not only to material being advanced by the belt 8 but also to material advancing down a slide or in free fall.

What is claimed is:

1. Apparatus for automatically inspecting matter, comprising emitting means serving to emit a detection medium, which comprises electromagnetic radiation, to be active at said matter, receiving means in the form of a rotary polygonal mirror arranged to receive from a multiplicity of detection zones at said matter detection medium which has been varied by variations in said matter, a plurality of detecting means serving to receive the varied medium by reflection from the mirror, to detect respective wavelengths of said varied medium substantially simultaneously, and to generate detection data in respect of said wavelengths substantially simultaneously and in dependence upon the variations in said medium, and data-obtaining means connected to said detecting means and serving to obtain said detection data therefrom, the arrangement being such that the beams of the varied medium which are received at said detecting means and emanate from the respective detection zones travel along respective paths from said matter to said mirror which paths converge continuously with respect to each other from said matter to said mirror and do not substantially co-incide with any significant part of the path of the emitted detection medium from the emitting means to the matter.

2. Apparatus according to claim 1, wherein said mirror is arranged to receive the varied medium directly from said matter.

3. Apparatus according to claim 1, and further comprising at least one planar mirror by way of which said beams travel from said matter to said rotary polygonal mirror.

4. Apparatus according to claim 1, wherein said emitting means is arranged to emit said medium in the form of a scanning beam which scans said detection zones.

5. Apparatus according to claim 1, wherein said emitting means emits said medium in the form of a plurality of scanning beams which are co-extensive with each other and which scan said detection zones.

6. Apparatus according to claim 1, wherein said detecting means comprises a plurality of detectors arranged to receive substantially simultaneously with each other the varied medium from, in turn, groups of detection spots whereof each group contains a plurality of detection spots and provides one of said detection zones.

7. Apparatus according to claim 1, and further comprising a camera arranged to detect spatial characteristics of individual objects of which said matter is comprised, and to generate further detection data in dependence upon the detected spatial characteristics, said data-obtaining means being arranged to employ the first-mentioned detection data to identify variations in the composition of said matter.

8. Apparatus according to claims 1, wherein said emitting means and said rotary polygonal mirror are arranged so as to be located at respective opposite sides of said matter, the apparatus further comprising shielding means arranged to prevent said detecting means from receiving the medium directly from said emitting means.

9. Apparatus according to claim 1, and further comprising a second rotary polygonal mirror arranged to receive detection medium which has been varied by variations in said matter, and second detecting means serving to receive the varied medium by reflection from said second rotary polygonal mirror, to generate other detection data in dependence upon the variations in said medium, said data-obtaining means being connected to said second detecting means and serving to obtain said other detection data therefrom.

10. Apparatus according to claim 9, wherein the arrangement is such that beams of the varied medium which are received at said second detecting means and emanate from respective detection zones travel along respective paths from said matter to said second rotary polygonal mirror which paths converge continuously with respect to each other from said matter to said second rotary polygonal mirror.

11. Apparatus according to claim 9, wherein the first-mentioned rotary polygonal mirror and the first-mentioned detecting means are parts of a first inspection arrangement, said second rotary polygonal mirror and said second detecting means are parts of a second inspection arrangement, and the first and second inspection arrangements are disposed side-by-side.

12. Apparatus according to claim 11, wherein said first and second inspection arrangements are respective modules.

13. Apparatus according to claim 1, and further comprising a detection station which comprises the rotary polygonal mirror and the detecting means and through which said matter advances in a feed direction.

14. Apparatus according to claim 13, wherein the rotary polygonal mirror has its axis of rotation at substantially the axis of its polygon and extending in said feed direction.

15. Apparatus according to claim 13 wherein said emitting means is arranged to emit said medium in the form of a scanning beam which scans said detection zones, and wherein the scanning beam scans said matter transversely of said feed direction.

16. Apparatus according to claim 13, wherein the arrangement is such that said matter falls freely through said detection station.

17. Apparatus according to claim 16, and further comprising distributing means arranged to cause said matter to fall freely in a curved distribution around a vertical axis.

18. Apparatus according to claim 17, wherein said distributing means is arranged to cause said distribution to be at a substantially constant radius from said vertical axis.

19. Apparatus according to claim 13 and further comprising a second rotary polygonal mirror arranged to receive detection medium which has been varied by variations in said matter, and second detecting means serving to receive the varied medium by reflection from said second rotary polygonal mirror, to generate other detection data in dependence upon the variations in said medium, said data-obtaining means being connected to said second detecting means and serving to obtain said other detection data therefrom, and wherein said feed direction is at an angle to the vertical and wherein the first-mentioned detection data and said other detection data are utilised to obtain an indication of height of a common zone of said matter.

20. Apparatus according to claim 1, wherein said emitting means serves to emit visible light as the detection medium, and wherein said data-obtaining means performs substantially simultaneous analysis of a plurality of wavelengths in the visible light spectrum.

21. A method of automatically inspecting matter, comprising emitting from emitting means a detection medium, which comprises electromagnetic radiation, to be active at said matter, said medium being varied by variations in said matter, receiving the varied medium from a multiplicity of detection zones at said matter at receiving means in the form of a rotary polygonal mirror, reflecting the varied medium from the mirror to a plurality of detecting means, detecting at said detecting means a plurality of discrete wavelengths of said varied medium substantially simultaneously, and generating detection data from said detecting means in respect of said plurality of discrete wavelengths substantially simultaneously and in dependence upon the variations in said medium, the beams of the varied medium which are received at said detecting means and emanate from the respective detection zones travelling along respective paths from said matter to said mirror which paths converge continuously with respect to each other from said matter to said mirror and do not substantially co-incide with any significant part of the path of the emitted detection medium from the emitting means to the matter.

22. A method according to claim 21, wherein said beams travel directly from said matter to said mirror.

23. A method according to claim 21, wherein said medium is emitted in the form of a scanning beam which scans said detection zones.

24. A method according to claim 21, wherein said medium is emitted in the form of a plurality of scanning beams which are substantially co-extensive with each other and which scan said detection zones.

25. A method according to claim 21, wherein each detection zone is in the form of a group of detection spots, and wherein the varied medium from all of the detection spots in each group is received substantially simultaneously at said rotary polygonal mirror.

26. A method according to claim 25, wherein said matter comprises granulates.

27. A method according to claim 21, wherein said matter comprises individual objects, said detection data is employed to identify variations in the composition of said matter, a camera is utilised to detect spatial characteristics of said objects, and further detection data is generated in dependence upon the detected spatial characteristics.

28. A method according to claim 27, wherein said spatial characteristics comprise profiles of the respective objects.

29. A method according to claim 27, wherein said spatial characteristics comprise relative positions of the objects.

30. A method according to claim 21, wherein at least part of the emitted medium passes through said matter and is received at said rotary polygonal mirror, and said detecting means is prevented from receiving the medium directly from said emitting means.

31. A method according to claim 21, wherein said medium is active at said multiplicity of detection zones while said matter is falling freely at a detection level.

32. A method according to claim 31, wherein said matter falls freely in a curved distribution around a vertical axis.

33. A method according to claim 32, wherein said distribution is at a substantially constant radius from said axis.

34. A method according to claim 21, wherein said matter includes an object surfaces of which are orientated differently from each other, said medium being varied in its intensity in dependence upon the respective orientations of said surfaces, and those variations in intensity produce detection data used to obtain an indication of a dimension of said object.

35. A method according to claim 21, wherein the detection medium is visible light and analysis of a plurality of wavelengths in the visible light spectrum is performed substantially simultaneously with each other upon the varied medium.

36. Apparatus for automatically inspecting matter, comprising emitting means serving to emit a detection medium, which comprises electromagnetic radiation, to be active at said matter, a rotary polygonal mirror arranged to receive directly from said matter detection medium varied by variations in said matter, detecting means serving to receive the varied medium by reflection from the rotary polygonal mirror, to detect a plurality of wavelengths of said varied medium substantially simultaneously, and to generate detection data in respect of said plurality of wavelengths substantially simultaneously and in dependence upon the variations in said medium, and data-obtaining means connected to said detecting means and serving to obtain said detection data therefrom, the arrangement being such that the path of the varied medium from the matter to the mirror does not substantially co-incide with any significant part of the path of the emitted detection medium from the emitting means to the matter.

37. Apparatus according to claim 36, and further comprising a detection station which comprises the rotary polygonal mirror and the detecting means and through which said matter advances in a feed direction, the mirror having its axis of rotation at substantially the axis of its polygon and extending in said feed direction.

38. Apparatus for automatically inspecting matter, comprising emitting means serving to emit a detection medium, which comprises electromagnetic radiation, to be active at said matter, a rotary polygonal mirror arranged to receive from a multiplicity of detection zones at said matter detection medium varied by variations in said matter, a planar mirror by way of which said rotary polygonal mirror receives the varied medium, detecting means serving to receive the varied medium by reflection from the rotary polygonal mirror, to detect a plurality of wavelengths of said varied medium substantially simultaneously, and to generate detection data in respect of said plurality of wavelengths substantially simultaneously and in dependence upon the variations in said medium, and data-obtaining means connected to said detecting means and serving to obtain said detection data therefrom, the planar being arranged to reflect varied medium from at least some of said multiplicity of detection zones.

39. A method of automatically inspecting matter comprised of differing materials, comprising emitting a beam of detection medium so that said beam scans said matter in a traversing manner, said medium being varied by variations in the composition of said matter, and one of by passing said medium through said matter and through being reflected from said matter, receiving the varied medium at detecting means, generating detection data from said detecting means in dependence upon the variations in said medium, and identifying at least one of said materials from said data.

40. A method according to claim 39, wherein said medium is varied through being reflected from said matter, and said detecting means is prevented from receiving direct reflection of the emitted beam.

41. A method according to claims 39, and further comprising emitting, co-extensively with said beam, a second beam of detection medium so that said second beam also scans said matter.

42. Apparatus for automatically inspecting matter comprised of differing materials, comprising emitting means serving to emit a scanning beam of detection medium to scan said matter in a traversing manner, receiving means arranged to receive detection medium varied by variations in the composition of said matter, detecting means serving to generate detection data in dependence upon the variations in said medium, and data-obtaining means connected to said detecting means and serving to obtain said detection data therefrom and to identify at least one of said materials from said data.

43. Apparatus according to claim 42, wherein said emitting means and said receiving means are arranged to be located at a common side of said matter, and said receiving means is off-set relative to a direct reflection path of said beam.

44. Apparatus according to claim 42, wherein said emitting means serves to emit, co-extensively with said beam, a second beam of detection medium to scan said matter.

45. A method of automatically inspecting matter for varying composition, comprising advancing a stream of said matter comprised of individual objects, emitting a detection medium to be active at a multiplicity of individual detection zones distributed across substantially the width of said stream at a transverse section of said stream, said medium being varied by variations in the composition of said matter at said transverse section, receiving the varied medium at receiving means, generating detection data in dependence upon the variations in said medium, utilising a camera, which is other than said receiving means, to detect spatial characteristics of said objects, and generating further data in dependence upon said spatial characteristics.

46. A method according to claim 45, wherein said spatial characteristics comprise profiles of the respective objects.

47. A method according to claim 45, wherein said spatial characteristics comprise relative positions of the objects.

48. Apparatus for automatically inspecting matter for varying composition, comprising detection station means through which a stream of said matter comprised of individual objects advances, emitting means serving to emit a detection medium to be active at a multiplicity of individual detection zones distributed across substantially the width of said stream at a transverse section of said stream at said station means, receiving means serving to receive detection medium varied by variations in the composition of said matter at said section, detecting means serving to generate a first series of detection data in dependence upon the variations in said medium, a camera, which is other than said receiving means, at said station means and serving to detect spatial characteristics of said objects and serving to generate a second series of detection data in dependence upon said spatial characteristics, and data-obtaining means connected to said detecting means and to said camera and serving to obtain the first and second series of detection data therefrom.

49. A method of automatically inspecting matter comprised of differing materials, comprising emitting a detection medium to be active at said matter, said medium being varied by variations in the composition of said matter, receiving the varied medium at receiving means from, in turn, groups of detection spots at said matter, whereof each group contains a plurality of said detection spots and provides one of a plurality of detection zones, with the varied medium from all of the detection spots in each group being received substantially simultaneously, generating: detection data for each detection zone in dependence upon the variations in said medium at the detection zone, and identifying at least one of said materials from said data.

50. A method according to claim 49, wherein said matter comprises granulates.

51. Apparatus for automatically inspecting matter comprised of differing materials, comprising emitting means serving to emit a detection medium to be active at said matter, receiving means serving to receive detection medium varied by variations in the composition of said matter from, in turn, groups of detection spots at said matter, whereof each group contains a plurality of said detection spots and provides one of a plurality of detection zones, with the varied medium from all of the detection spots in each group being received substantially simultaneously, detecting means serving to generate detection data in dependence upon the variations in said medium at each detection zone, and data-obtaining means connected to said detecting means and serving to obtain said detection data therefrom and to identify at least one of said materials from said data.

52. Apparatus for automatically inspecting a stream of matter, comprising emitting means serving to emit a detection medium to be active at said matter, first and second receiving means of respective first and second inspection arrangements separate from each other and arranged to receive from said matter detection medium varied by variations in said matter, first and second detecting means of said respective first and second inspection arrangements serving to receive the varied medium by reflection from the receiving means, and to generate detection data in dependence upon the variations in said medium, and data-obtaining means connected to said first and second detecting means and serving to obtain said detection data therefrom, the apparatus being such that the inspection paths of the respective inspection arrangements are substantially aligned with each other transversely of the stream to form, a substantially continuous inspection path.

53. Apparatus according to claim 52, wherein the first and second inspection arrangements are disposed side-by-side.

54. Apparatus according to claim 52, wherein said inspection paths of the respective inspection arrangements substantially co-incide at least partly with each other.

55. Apparatus for automatically inspecting a stream of matter, comprising emitting means serving to emit a detection medium, which comprises radiation, as a scanning beam to irradiate in a traversing manner a path over said matter, inspecting means arranged to inspect the irradiated path at an oblique angle to said matter, and ascertaining means arranged to ascertain from that inspection the general profile of that path.

56. A method of inspecting a stream of matter, comprising emitting from emitting means a detection medium, which comprises radiation, to be active at said matter, said medium being varied by variations in said matter, at least part of the emitted medium passing through said matter and the varied medium which has passed through said matter being received at detecting means at a diametrically opposite side of said stream to said emitting means, and preventing said detecting means from receiving the medium directly from the emitting means.

57. A method according to claim 56, wherein the detection medium is visible light and analysis of a plurality of wavelengths in the visible light spectrum is performed substantially simultaneously with each other upon the varied medium.

58. Apparatus for inspecting matter, comprising emitting means serving to emit a detection medium, which comprises radiation, to be active at said matter, detecting means arranged to receive, by passage of the medium through said matter, detection medium varied by variations in said matter, and shielding means arranged to prevent the detecting means from receiving the medium directly from the emitting means and located on a direct path from the emitting means to the detecting means.

59. Apparatus according to claim 58, and further comprising receiving means located between said emitting means and said detecting means and through which the varied medium is arranged to pass, said receiving means comprising a Fresnel lens.

* * * * *